United States Patent [19]

Engel et al.

[11] Patent Number: 4,704,387

[45] Date of Patent: Nov. 3, 1987

[54] N-BENZYL, PHENETHYL, METHOXYETHYL OR ALLYL SUBSTITUTED BENZYLPHTHALAZINONES HAVING ANTIALLERGIC AND ANTIHISTAMINE ACTION

[75] Inventors: Jürgen Engel, Alzenau; Gerhard Scheffler, Hanau, both of Fed. Rep. of Germany

[73] Assignee: ASTA-Werke Aktiengesellschaft, Chemische Fabrik, Bielefeld, Fed. Rep. of Germany

[21] Appl. No.: 764,995

[22] Filed: Aug. 12, 1985

[30] Foreign Application Priority Data

Sep. 14, 1984 [DE] Fed. Rep. of Germany ....... 3433776

[51] Int. Cl.[4] .................... A61K 31/55; C07D 403/04; C07D 223/12; C07D 237/32

[52] U.S. Cl. .................................... 514/212; 540/598; 544/357

[58] Field of Search ..................... 544/357; 260/243.3; 514/212; 540/598

[56] References Cited

U.S. PATENT DOCUMENTS

| | | | |
|---|---|---|---|
| 3,753,988 | 8/1973 | Rodway et al. | 540/599 |
| 3,813,384 | 5/1974 | Vogelsang | 544/239 |
| 3,845,052 | 10/1974 | Stachel et al. | 540/598 |

FOREIGN PATENT DOCUMENTS

| | | | |
|---|---|---|---|
| 164593 | 10/1985 | European Pat. Off. | 544/237 |
| 2164058 | 7/1972 | Fed. Rep. of Germany . | |

OTHER PUBLICATIONS

Vogelsang et al, Chem. Abst. 77-126670b.

Tatsumi et al, Chem. Abst. 103-153203p.

*Primary Examiner*—Donald G. Daus

*Assistant Examiner*—Cecilia Shen

*Attorney, Agent, or Firm*—Cushman, Darby & Cushman

[57] ABSTRACT

Compounds of the formula

I wherein R is a benzyl group, a phenylethyl group, a methoxyethyl group or an allyl group having an antiallergic activity.

11 Claims, No Drawings

N-BENZYL, PHENETHYL, METHOXYETHYL OR ALLYL SUBSTITUTED BENZYLPHTHALAZINONES HAVING ANTIALLERGIC AND ANTIHISTAMINE ACTION

BACKGROUND OF THE INVENTION

German Pat. No. 2164058 is directed to basic substituted 4-benzyl-1-(2H)-phthalazinone derivatives of the following formula

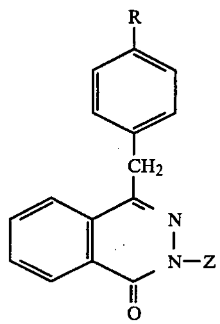

wherein R is a hydrogen or halogen atom, a trifluoromethyl group, or a lower alkyl or alkoxy group and Z is a 4-perhydroazepinyl, N-methyl-4-perhydroazepinyl, 3-quinuclidyl, 3-tropanyl, 3-nortropanyl, N-methyl-3-pyrrolidinyl or N-methyl-2-pyrrolidinyl-methyl group, as well as the physiologically compatible acid addition salt. These compounds have an antihistamine action.

SUMMARY OF THE INVENTION

The invention is directed to substituted benzylphthalazinone derivatives of the formula

I

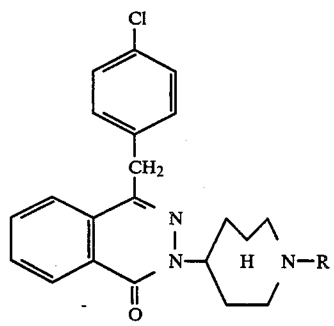

wherein R is a benzyl group, a phenylethyl group, a methoxyethyl group or an allyl group or a physiologically compatible acid addition salt thereof.

There is also included a process for the production of a substituted benzylphthalazinone derivative of the formula

I

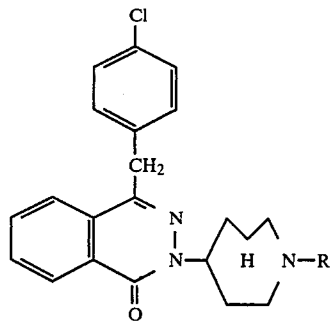

wherein R is a benzyl group, a phenylethyl group, a methoxyethyl group or an allyl group or a physiologically compatible acid addition salt thereof comprising:

(a) reacting a compound of the formula

II

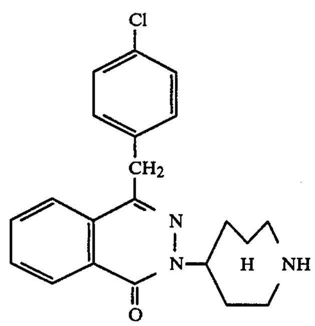

with a compound of the formula

RX (III)

wherein R is defined as in formula I and X is a hydroxy group esterified with a strong inorganic or organic acid or (b) a compound of the formula

IV

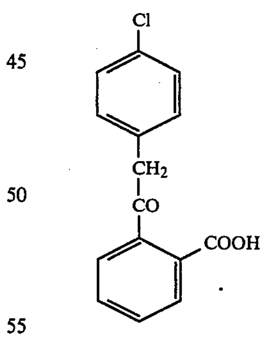

or a reactable derivative thereof is reacted with a hydrazine of the general formula:

$H_2N—NH—Z$ (V)

wherein Z is hydrogen or the group

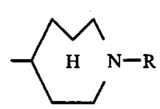

and R is as defined in formula I, with the proviso that where Z is hydrogen the benzyl-phthalazinone derivative obtained is subsequently reacted with a compound of the formula:

Y—Q VI wherein Y is a halogen atom, e.g. chlorine, bromine or iodine, or a sulfonic acid ester group, e.g. the methyl or ethyl ester, and Q is either the group

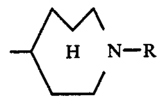

or the group

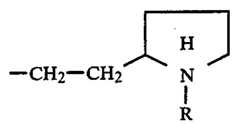

and R is as previously defined, and optionally the compound obtained is converted into its acid addition salt.

The invention is also directed to the use of the compounds of formula I as therapeutically active materials.

Also the invention is directed to medicines containing a compound of formula I in addition to a customary carrier and/or diluent and/or adjuvant.

The invention also includes a process for the production of a medicine comprising working a compound of general formula I with a customary carrier and/or diluent or other adjuvant to a pharmaceutical preparation or bringing it into a therapeutically usable form.

Finally the invention also includes the use of the compounds of general formula I for the production of medicines.

The compounds of the invention are antiallergic and asthma prophylactically active, however, considerably stronger and better than the known compounds of German Pat. No. 2164058. Furthermore, in contrast to the known medicine AZELASTIN (compound according to Example 5 of German Pat. No. 2164058) they have either no, or a considerably less, bitter taste, so that they can be applied for example even as an aerosol.

In regard to process (a)

The process can be carried out without additional solvent or in a suitable solvent or dispersing agent. As solvent or dispersing agent for example there are included: aromatic hydrocarbons such as for example benzene, mesitylene, toluene, xylene, pyridine, lower aliphatic ketones such as for example acetone, methyl ethyl ketone, halogenated hydrocarbons such as for example chloroform, 1,2-dichloroethane, carbon tetrachloride, chlorobenzene, methylene chloride, ethers such as for example tetrahydrofurane, dioxane, diisopropyl ether, sulfoxides such as for example, dimethylsulfoxide, tertiary acid amides such as for example dimethyl formamide, dimethyl acetamide, hexamethyl phosphoric acid triamide, tetramethylurea, N-methyl pyrrolidone, lower alcohols such as for example methanol, ethanol, isopropanol, amyl alcohol, butanol, tert-.butanol as well as mixtures of the agents mentioned. The reaction is carried out for example at temperatures between 20° to 200° C., preferably 40° to 160° C. or even 50° to 120° C. If a solvent or dispersing agent is used, frequently one operates at the reflux temperature of the agent. The reaction frequently runs even at room temperature, or at a temperature between 40° to 120° C.

The reaction is advantageously carried out in the presence of acid binding agents such as alkali carbonates, e.g. sodium carbonate or potassium carbonates, alkali acetates, e.g. sodium acetate or potassium acetate, alkali hydroxides, e.g. sodium hydroxide or potassium hydroxide or tertiary bases (triethylamine, pyridine).

In the event that X is an esterified hydroxyl group then it is a matter of a reactable ester. A reactable ester thereby for example is one of a strong organic or inorganic acid, such as above all, a hydrogen halide, for example hydrochloric acid, hydrobromic acid, hydroiodic acid, or a sulfonic acid,, such as an aryl or $C_1$-$C_6$-alkylsulfonic acid, for example lower alkybenzenesulfonic acids (p-toluenesulfonic acid). As solvents there are especially considered agents such as dioxane/ water, dimethylformamide/water or lower saturated aliphatic alcohols, e.g. those mentioned above.

Unknown starting materials of Formula III can be obtained for example analogous, Houben-Weyl, Methoden der Organischen Chemie, Volume 5/3 (1962), page 503 et seq., Volume 6/2 (1963) page 475 et. seq or Volume 9 (1955) page 426.

In regard to (b)

As derivatives of the carboxylic acids of general formula IV which are capable of reaction there are especially considered acid halides (chloride, bromide, iodide), esters (especially with $C_1$-$C_6$-alkanols) and anhydrides (for example p-chloro-benzylidene phthalide). The reaction is carried out in the presence or absence of the customary solvents and assistants at temperatures between 40° and 200° C. and in a wide pH range from acid to alkaline.

As solvents there are suited for example, water, aromatic hydrocarbons such as for example benzene, mesitylene, toluene, xylene, halogenated hydrocarbons such as for example chloroform, 1,2-dichloroethane, carbon tetrachloride, chlorobenzene, methylene chloride, ethers such as for example tetrahydrofurane, dioxane, diisopropyl ether, sulfoxide such as for example dimethyl sulfoxide, tertiary acid amides such as for example dimethyl-formamide, dimethyl-acetamide, hexamethyl-phosphoric acid, triamide, tetramethyl-urea, urea, N-methyl pyrrolidone; lower alcohols such as for example methanol, ethanol, isopropanol, amyl-alcohol, butanol, tert.butanol and mixtures of the agents mentioned as well as also tertiary amines, for example pyridine. As assistants there can be employed bases, acids and condensation agents conventional for these reactions.

For the reaction of those benzyl-phthalazinone derivatives which are obtained if Z of formula V is hydrogen with a compound Y-Q likewise there are employed the above-mentioned solvents as well as the above-mentioned temperature range.

Especially there are employed as solvent tertiary and amides (for example dimethyl-formamides), aromatic hydrocarbons (for example toluene or even water, whereby frequently the operation is carried out in the presence of basic material (for example alkali hydroxides). Preferably operation is at temperatures between 80°-200° C., especially 80°-150° C.

In the event Y of formula VI is a halogen atom it is chloride, bromine or iodine. In the event Y of formula VI represents a sulfonic acid ester group, it is for example a $C_1$-$C_6$-alkylsulfonic acid group (for example $CH_3$—$SO_2$—O— an arylsulfonic acid group, such as for example the radical of a $C_1$-$C_4$-alkylbenzenesulfonic acid (for example a p-toluenesulfonyloxy group).

The benzyl-phthalazinone starting compound (compounds of formula I where there is a hydrogen atom located on the acidamide nitrogen atom in place of the seven member ring having the substituents) for example is also employed in the form of its alkali salt (Na/K). This type of alkali salt can be obtained for example in customary manner from the corresponding phthalazinone and the alkali metal in alcoholic solution (for example ethanol) or in another customary agent for this at 60° to 100° C. The end products obtained by the reaction with compounds of formula VI in a given case represent at times mixtures of compounds of formula I (having the 7 member ring) and the corresponding compounds which in place of the 7 member ring contain the group

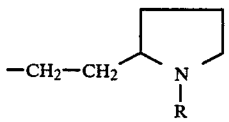

(cycloammonium rearrangement with change of size of the ring. The isolation of the sought for compound I and of the 5 member ring compound for example can be carried out in customary manner by fractional crystallization.

Depending on the process condition and starting materials there is obtained the end product of formula I in free form or in the form of its salt. The salt of the end product can again be converted into the base in known manner, for example with alkali or ion exchangers. From the latter (free base) salts can be obtained by reaction with organic or inorganic acids, especially those which are suited for the formation of therapeutically usable salts, e.g. hydrochloric acid, sulfuric acid, phosphoric acid, acetic acid, maleic acid, p-toluenesulfonic acid.

The compounds of the invention of formula I contain an asymmetric carbon atom (C-atom of the 7 member ring which is connected with the acid amide nitrogen atom of the phthalazinone) and therefore as a rule are obtained as the racemate. Such racemates can be resolved into the optically active isomers in known manner for example by fractional crystallization of the salts of a racemic compound I with optically active acids or also by chromatographic separation of the racematic (see for example Angewandte Chemie 92/1 (1980), page 14). However, it is also possible to initially employ an optically active starting material in which case then as end product there is obtained a corresponding optically active form.

The present invention thus includes both the racemate and the corresponding optically active dextro and laevo rotating forms.

The compounds of the invention are suitable for the production of pharmaceutical compositions or preparations. The pharmaceutical compositions or medicines contain as active material one or more of the compounds of the invention, optionally in admixture with other pharmacologically or pharmaceutically active materials. The production of the medicines can be carried out with use of known and customary pharmaceutical carriers and adjuvants.

The compositions can comprise, consist essentially of, or consist of the stated materials and the processes can comprise, consist essentially of, or consist of the steps set forth with the recited materials.

DETAILED DESCRIPTION

EXAMPLE 1

4-(4-chlorobenzyl)-2-(hexahydro-1-benzyl-azepin-4-yl)-1-(2H)-phthalazinone (formula I, R=benzyl)

There were dropped into a mixture of 6 grams (0.013 mole) of 4-(4-chlorobenzyl)-2-(hexahydro azepin-4-yl)-1 (2H)-phthalazinone×HBr in 60 ml of dioxane heated to 50° C., 3.2 grams (0.031 mole=4.4 ml) of triethylamine and subsequently 1.7 grams (0.013 mole=1.5 ml) of benzyl chloride with stirring. After the end of the addition the reaction mixture was stirred for 5 hours at 90° C. After cooling the precipitated ammonium salt was filtered off with suction. The reaction solution was thereupon concentrated to dryness in a vacuum. The residue was recrystallized twice from isopropanol: crystals of M.P. 140°-141° C. Yield: 3.1 grams (51%).

The starting material is obtained for example as follows:

60 grams (0.157 mole) of 4-(p- chlorobenzyl)-2-(hexahydroxy-1-methyl azepin-4-yl)- 1-(2H)-phthalazinone were dissolved with heating to 95° C. in 600 ml of dried toluene. Subsequently there were dropped in with stirring 51.1 grams (0.471 mole=45 ml) of ethyl chloroformate in 45 ml of toluene. The mixture was stirred for 5 hours at 95° C. After cooling to room temperature the reaction mixture was filtered off with suction from the insolubles and concentrated on a rotary evaporator. There remained an oily residue which triturated with a little ether precipitated as a white crystalline product and melted at 103° to 105° C. (Yield: 53.4 grams (77%).

53.4 grams (0.12 mole) of the thus obtained 1-carboxyethyl derivative (formula I, R=$COOC_2H_5$) and 114 ml of a 40% solution of hydrogen bromide in glacial acetic acid heated at 85°-90° C. for 4 hours with intensive stirring, with increasing heating the carboxyethyl compound went into solution. After cooling the solution was concentrated in a vacuum. There was obtained from the viscous, oily residue by recrystallization from methanol the starting compound of formula I, wherein R is hydrogen, in the form of the white, crystalline hydrobromide. The mixture was filtered off with suction, washed several times with methanol and dried in a vacuum, M.P. 138°-140° C. Yield: 51 grams (95%).

EXAMPLE 2

4-(4-Chlorobenzyl)-2-(hexahydro-1 phenethyl-azepin-4 yl)-1-(2H)-phthalazinone (formula I, R=phenylethyl)

There was present a solution of 7 grams (0.015 mole) of 4- (4-chlorobenzyl)-2-(hexahydro-azepin-4-yl)-1-(2H)-phthalazinone×HBr in 60 ml of dioxane heated to 50° C. Subsequently there were dropped in with stirring 3.8 grams (0.037 mole=5.2 ml) of triethylamine and 2.9 grams (0.015 mole) of 2-bromoethyl benzene and the mixture stirred for 9 hours at 90° C. After cooling the precipitated salt was filtered off with suction and the solution concentrated on a rotary evaporator. The brown oily residue was chromatographed over a silica gel column (elution medium: diethyl ether/methanol=70:30) for rectification. The desired fractions were combined and the solvent distilled off in a vacuum. The residue was treated with 5 ml of isopropanol/HCl and 30 ml of ether. The hydrochloride thereupon precipitated as a viscous mass. The supernatant solution was decanted, the remaining residue dissolved in a little methyl-ethyl ketone and ether added *until slight turbidity. The hydrochloride which crystal*lized out overnight at room temperature was filtered off with suction, washed with methyl-ethyl ketone and dried in a vacuum. M.P. of the hydrochloride 173°-176° C. Yield 2.6 grams (34%).

EXAMPLE 3 .

4-(4-Chlorobenzyl)-2-(hexahydro-1-methoxyethyl-azepin-4-yl)-1-(2H)-phthalazinone (formula I, R=methoxyethyl)

6 grams (0.013 mole) of 4-(4-chlorobenzyl)-2-(hexahydroazepin-4-yl)-1-(2H)-phthalazinone× HBr were stirred together with 3.6 grams (0.026 mole) of $K_2CO_3$, 7.4 grams (0.078 mole=7.1 ml) of 2-chloroethyl methyl ether and 30 ml of dimethylacetamide for 2½ hours at an oil bath temperature of 120° C. Subsequently the mixture was cooled to room temperature and filtered off with suction from the insolubles. The solution was concentrated in a vacuum and the brownish oil obtained chromatographed by means of a silica gel column (elution agent: $CH_2Cl_2/CH_3OH$=90:10). The desired fractions were combined and the solvent distilled off on the rotary evaporator. The oily residue was made acid with isopropanol/HCl. The hydrochloride was precipitated as a viscous mass by addition of ether. After decanting off the supernatant solution the residue was triburated with methyl ethyl ketone at boiling heat, whereby the desired hydrochloride was obtained as a crystalline product. M.P. 194°-197° C. Yield: 1.8 grams (28%).

EXAMPLE 4

4-(4-Chlorobenzyl)-2-(hexahydro-1-allylazepin-4-yl)-1-(b 2H)-phthalazinone (formula I, R =allyl)

There were added to a solution of 6 grams (0.013 mole) of 4-(4-chlorobenzyl)-2-(hexahydroazepin-4-yl)-1-(2H)-phthalazinone×HBr in 60 ml dioxane heated to 50° C., 3.2 grams (0.003 mole=4.4 ml) of triethylamine and subsequently with stirring 1.6 grams (0.013 mole=1.15 ml) of allyl bromide. After the addition was carried out the mixture was stirred for an additional 2 hours at a temperature of 60° C. Subsequently the reaction mixture was filtered and the solvent distilled off in a vacuum. The oily residue obtained was dissolved in isopropanol/HCl at room temperature and this solution treated with ether up to slight turbidity. The hydrochloride crystallized out overnight. This was filtered off with suction followed by washing with isopropanol and dried in a drying oven. M.P. of the hydrochloride 123° C. Yield: 2.7 grams (45%).

The compounds of the invention show a good antiallergic and antihistamine action with the allergic and non-allergic setting free of histamine on rabbit leucocytes and rat peritoneal mast cell. The non-allergic setting free of histamine is released by a material which opens up the calcium channels in the mast cell membranes or leucocyte membranes and through this effects a release of histamine (for example Ca-Inophor A 23187).

For example there is obtained in the above-mentioned experimental method at a dosage of 0.3 mg/kg body weight with guinea pigs a 50% checking of the asthma attacks.

This antiallergic action is comparable with the action of the known medicine "Azelastine". The lowest effective dosage in the above-mentioned animal experiments for example is 0.03 mg/kg orally 0.01 mg/kg intravenously As a general dosage range for the action (animal experiments as above) is for example 0.3-3.0 mg/kg orally 0.1-1.0 mg/kg intravenously Indication for which the compounds of the invention can be taken in consideration: allergic asthma, allergic rhinitis.

The pharmaceutical preparations generally contain between 0.1 to 10, preferably up to 5 mg of the active components.

The dispensation for example can be carried out in the form of tablets, capsules, pills, dragees, plugs, salves, gels, creams, powders, dust powders, aerosols or in liquid form. As liquid forms of use there can be used for example oily or alcoholic or aqueous solutions, as well as suspensions and emulsions. Preferred forms of use are tablets which contain between 0.5 and 5 mg or solutions which contain 0.1 to 3% of an active material.

The individual dosages of the active components according to the invention can be for example:

(a) in oral forms of medicine between 0.5-5 mg, preferably 2 mg,
(b) in parenteral forms of medicine (for example intravenous, intramuscular) between 0.1-1 mg, preferably 0.5 mg,
(c) in forms of medicines for inhalation (solutions or aerosols) between 0.5 and 2 mg),
(d) in forms of medicine for local application to the skin and mucous membranes (for example in the form of solution, lotions, emulsions, salves, etc) between 1 and 5 mg, preferably 2 mg.

(The doses in each case are based on the free base).

For example, there can be reocmmended 1 to 2 tablets having an active material content of 0.5 to 5 mg three times a day or for example in intravenous injection an ampoule having a content of 1 to 2 ml with 0.5 to 5 mg of material one to two times a day. The maximum daily dosage in oral dispensation should not exceed 10 mg.

In treating dogs and cats the individual dosage orally is generally between approximately 0.5 and 5.0 mg/kg body weight; the parenteral dosage is between approximately 0.3 and 3.0 mg/kg body weight.

In treating horses and cattle the individual oral dosage is generally between approximately 0.3 and 3.0 mg/kg body weight.

The acute toxicity of the compounds of the invention on the mouse (expressed by LD50 mg/kg, method of Miller and Tainter: Proc. Soc. Exper. Biol. and Med. Vol. 57 (1944) page 261) for example in oral application is above 200 mg/kg.

The medicines can be used in human medicine, verterinary medicine as well as in agriculture alone or in admixture with other pharmacologically active materials.

Examples of Galenical Preparation

EXAMPLE I (Capsules)

50 grams of active material according to Example 1 were mixed with 350 grams of microcrystalline cellulose, 590 grams of lactose and 10 grams of magnesium stearate. The mixture was filled into size 3 hard gelatin plug capsules in each can there being used an amount of 100 mg.

EXAMPLE II (Tablets)

50 grams of active material according to Example 1 were mixed with 350 grams of microcrystalline cellulose, 590 grams of lactose and 10 grams of magnesium stearate. This mixture was pressed into bicomex tablets having a weight of 100 mg, a diameter of 6 mm and a radius of curvature of 5 mm.

The tablets can subsequently be coated according to customary process with a gastric juice permeable or soluble film.

EXAMPLE III (Ampoules For Injection and Inhalation)

10 grams of active material according to Example 1 were dissolved in 400 ml of ethanol and the solution filled up to 4 liters by addition of water for injection purposes. The solution was filtered sterilely through a membrane filter of suitable pore size. The filtrate was filled under aseptic conditions to 2 ml in ampoules. The ampoules were subsequently sterilized for 20 minutes in superheated steam at 121° C. for 20 minutes.

An ampoule contains 5 mg of active material in 2 ml of solution.

What is claimed is:

1. A substituted benzylphthalazinone. of the formula

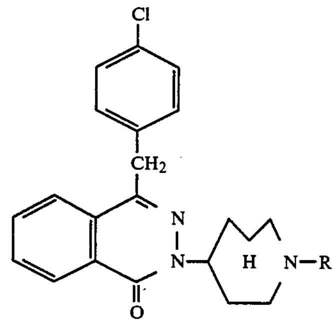

wherein R is a benzyl group, a phenylethyl group, a methoxy-ethyl group or an allyl group or a physiologically compatible acid addition salt thereof.

2. A substituted benzylphthalazinone according to claim 1 wherein R is a benzyl group.

3. A substituted benzylphthalazinone according to claim 1 wherein R is a phenylethyl group.

4. A substituted benzylphthalazinone according to claim 2 wherein R is a methoxyethyl group.

5. A substituted benzylphthalazinone according to claim 1 wherein R is an allyl group.

6. A pharmaceutical composition for suppressing the liberation of histamine comprising an effective antiallergic, antihistaminic amount of a compound according to claim 1 and a pharmaceutical adjuvant.

7. A process of supressing the liberation of histamine comprising administering to a mammal an amount of a compound of claim 1 effective for such purpose.

8. A process according to claim 1 where R is a benzyl group.

9. A process according to claim 6 where R is a phenethyl group.

10. A process according to claim 6 where R is a methoxyethyl.

11. A process according to claim 6 where R is an allyl group.

* * * * *